United States Patent [19]

Graef

[11] Patent Number: 4,853,086

[45] Date of Patent: Aug. 1, 1989

[54] HYDROPHILIC CELLULOSE PRODUCT AND METHOD OF ITS MANUFACTURE

[75] Inventor: Peter A. Graef, Tacoma, Wash.

[73] Assignee: Weyerhaeuser Company, Tacoma, Wash.

[21] Appl. No.: 941,461

[22] Filed: Dec. 15, 1986

[51] Int. Cl.$^4$ .............................................. D21H 3/02
[52] U.S. Cl. ................................. 162/157.6; 162/158; 162/182; 162/184; 604/375
[58] Field of Search ............... 162/9, 158, 157.6, 182, 162/184; 8/116.4; 604/375

[56] References Cited

U.S. PATENT DOCUMENTS

| | | | |
|---|---|---|---|
| 2,285,490 | 6/1942 | Broderick | 162/158 |
| 3,069,311 | 12/1962 | Harpham et al. | 162/157.6 |
| 3,224,926 | 12/1965 | Bernardin . | |
| 3,434,918 | 3/1969 | Bernardin . | |
| 3,932,209 | 1/1976 | Chatterjee | 162/157.6 |
| 4,035,147 | 7/1977 | Sangenis et al. | 162/157.6 |
| 4,472,167 | 9/1984 | Welch | 8/116.4 |

FOREIGN PATENT DOCUMENTS 806352 2/1969 Canada .
813616 5/1969 Canada .

OTHER PUBLICATIONS

Noller, Carl R., *Chemistry of Organic Compounds*, W. B. Saunders, p. 847, Philadelphia (1965).
Tesoro, G. C. and J. J. Willard in *Cellulose and Cellulose Derivatives*, Part V, Norbert M. Bikales and Leon Segal, eds: 837, 838, and 1209, Wiley-Interscience, New York (1971).

*Primary Examiner*—Peter Chin

[57] ABSTRACT

The present invention is a method of making a resilient hydrophilic cellulosic pulp particularly suitable for conversion into an absorbent fluff for products such as disposable diapers. The process involves treating a wet or partially dried cellulosic fiber web with an aqueous solution of a glycol and dialdehyde. Glyoxal and propylene glycol are preferred materials. These are desirable sprayed on a wet or only partially dried sheet at some convenient location on a conventional paper machine. This location is not critical, but a point about midway through the press section has given excellent results. The treated sheet is then dried conventionally. There is no need for the use of any catalysts or for a prolonged curing step at elevated temperatures. The products of the invention are characterized by a much increased absorbency rate and by a somewhat higher water holding capacity. The sheets also require less power for milling into a fibrous fluff. Knots or fiber clumps are reduced and there is no significant increase in fiber fines due to embrittlement of the treated pulp product. The invention further includes the products made using the present method.

7 Claims, No Drawings

HYDROPHILIC CELLULOSE PRODUCT AND METHOD OF ITS MANUFACTURE

BACKGROUND OF THE INVENTION

The present invention is a method of forming a resilient hydrophilic cellulose-based product and the products formed by the method. The method is especially directed to the formation of a sheeted pulp product that can be mechanically formed into a fibrous fluff having increased water absorption rate and water holding capacity. The product is especially useful for making articles such as disposable diapers and sanitary napkins.

Approximately 35 billion disposable infant diapers are presently manufactured worldwide each year. Each diaper contains an average weight of about 50 g of fluffed cellulosic fiber. Worldwide it is estimated that about 2 million tons of wood pulp are used in absorbent products of all types. Besides infant diapers these include sanitary napkins and tampons, adult incontinent pads and numerous other products such as bed pads, wipes and towelettes. All of the above products have had a rapid technical evolution over the past decade. However, little or nothing has been changed in the wood pulp products which are fiberized to form the essential absorbent fluff in this group of products. It is evident that there is an enormous market potential for fluff pulps that would be more effective absorbents if they could compete economically with presently available materials.

It has been known for many years that it is possible to make cellulosic materials for absorbent fluffs which have more rapid liquid pickup and greater liquid retention under pressure. As one example, U.S. Pat. No. 3,224,926 to Bernardin describes treatment of a cellulosic material, such as sheeted wood pulp, with a crosslinking agent such as formaldehyde or dimethylolurea. The impregnated pulp is dried to about 10% moisture, then fluffed. After fluffing, it is heated to 110°-150° C. for a sufficient time to effect curing. The fiber is said to be useful for making articles such as filter media, cushioning, and absorbent products such as sanitary napkins and wipes.

In a somewhat related process, the same inventor in U.S. Pat. No. 3,434,918 describes a paper sheet in which a portion of the furnish has been treated with a crosslinking agent such as those just noted. Preferably one portion of the fiber is treated in sheeted form with a crosslinking agent and curing catalyst. This is wet aged to insolubilize the crosslinker, then redispersed and mixed with untreated fiber. The mixture is again sheeted on a papermaking machine. As part of this process, the sheet is subsequently creped in a conventional manner on a Yankee dryer. Final cure of the product is effected by raising the sheet temperature to about 150° C. for a short period of time. Finished sheets are suggested for use as wipes, toweling and tissues and may be further useful in diapers.

In another patent to the same inventor, Can. 813,616, the invention is directed toward a creped sheet having nearly circular absorption properties. The furnish is a mixture of collapsed fiber, which is dry crosslinked, and conventional fibers. The crosslinked fiber must be treated, air dried, fluffed and heat cured at about 130°-135° C. prior to mixing with the conventional papermaking fibers.

Van Haaften in Can. 806,352 discloses an invention directed to pads, such as sanitary napkins and diapers, which contain a layer of crosslinked fiber overlying or surrounding a second layer of conventional cellulose fluff. This construction is said to give better flow control and reduce surface spreading of wetness.

The above noted and other crosslinking materials have long been used for treatment of textiles for giving properties such as wrinkle and crease resistance. Virtually all of the popular wash and wear fabrics contain cellulosic fiber which has been crosslinked in some manner. Welch, in U.S. Pat. No. 4,472,167, describes treatment of cotton textiles with glyoxal and glycols. A glyoxal and a glycol are co-reacted with cellulose in a the presence of an aluminum sulfate catalyst and an alpha-hydroxyacid; e.g., tartaric or citric acid. The latter material serves as a catalyst activator. The treated textile must contain at least 30% cellulose fiber, but the invention is also said to apply to nonwoven textiles and paper. A critical part of the invention is drying the product and heating to a temperature of 110°-135° C. for 0.5-5 minutes.

Noller, *Chemistry of Organic Compounds*, 3rd Ed.: 847, W.B. Saunders Company, Philadelphia (1965) notes that glyoxal can be used for shrinkproofing rayon fabrics. This apparently works by crosslinking cellulose chains through the formation of cyclic acetals. Glyoxal is also said to increase the wet strength and absorbency of paper. A heat curing step above 100° C. under dry conditions is implicit in the above treatment.

Tesoro and Willard in *Cellulose and Cellulose Derivatives*, Part V, Norbert M. Bikales and Leon Segal, eds.: 837-838, Wiley-Interscience, New York (1971) also not that glyoxal can be reacted with cellulose under conditions similar to those used for the reaction of formaldehyde. Glyoxal and other dialdehydes were tried, apparently unsuccessfully, to offset the serious strength losses associated with formaldehyde crosslinking of cellulosic fabrics.

While processes direct to making crease resistant fibers have been very successful commercially, none of the others described above appear to have advanced beyond the stage of laboratory curiosities. This is particularly the case for treatments involving wood pulp. One or both of two major stumbling blocks have remained in the way of commercial acceptance of so-called crosslinked fibers for use in absorbent products such as diapers. In all cases a heat curing step carried out well above 100° C. for some significant length of time has been required. In some cases this has involved heat treatment of a sheeted product and in other cases, heat treatment of a sheet product which has subsequently been fluffed. To date there has been no practical way found to do this on a paper machine without a major loss in production capability. Similarly, the problem of heat curing treated fluff at the point of production or point of use has not been resolved. A further problem was only hinted at in the above cited article by Tesoro et al. This is the serious matter of embrittlement and discoloration of crosslinked fibers. To the present time no fibers which have been crosslinked in sheeted form have been suitable for subsequent conversion to fluff because of serious fiber breakage during the fluffing process. This results in an unacceptable amount of fine material. The problem of fluffing an uncured pulp and subsequently heat curing in a diaper plant was mentioned previously. The additional burden and expense that heat curing a fluff pulp would place upon a diaper manufacturer is one that to date they have been unwilling to assume. For these reasons, despite their known advantages, crosslinked pulps have found essentially no commercial application in absorbent sanitary products.

It might be noted that there is still considerable controversy among cellulose chemists as to whether materials such as dimethylolureas or glyoxal actually serve as crosslinking or briding agents between adjacent cellulose molecules or whether some other reaction occurs. Whatever the nature of the reaction, it is immaterial to the present invention where all of the problems noted above have been successfully overcome in a convenient and economical manner.

SUMMARY OF THE INVENTION

The present invention comprises a method of making a resilient hydrophilic cellulosic sheeted pump product. The method further includes defiberizing the dried treated sheet and air felting the resulting fiber into an absorbent fluff product. The invention also should be considered to include the absorbent fluff and products which incorporate it. The product has the capability of being mechanically formed into a fibrous fluff having a significantly increased water absorption rate when compared with untreated pulp. The method comprises sheeting a fibrous cellulosic material from an aqueous slurry into a fibrous web. This web is then treated with an aqueous solution of a glycol and dialdehyde. The glycol is of the type $HO-[(CH_2)_mO]_n-H$ where m is 2 or 3 and n is in the range of 1–500, and the dialdehyde is of the type $OCH-(CHX)_n-CHO$ where n is the range of 0–4 and X is hydrogen or hydroxyl. The glycol is present and applied to the sheeted fibrous web in an amount in the range of 5–50 kg/t of dry fiber and the dialdehyde is similarly applied in the range of 5–50 kg/t. After application of the glycol and dialdehyde solution to the sheeted fibrous web, the web is dried to a moisture content in the range of about 1–20%, preferably about 3–12%.

Most preferably the temperature of the treated web will not be allowed to exceed about 100° C. during drying. This is important for two reasons. First, it enables production of the product at essentially normal rates on conventional papermaking equipment. Second, it prevents embrittlement and discoloration of the fiber when the sheet is ultimately formed into a fluff product. The sheeted product is readily defibered without the formation of an excessive amount of fine material.

The results obtained by drying under normal papermaking conditions without any catalyst present are quite surprising in view of all of the teachings of the prior art which indicate that a product of this type should be crosslinked under strongly acidic conditions and at high temperatures which are not readily attainable on conventional papermaking equipment. As noted beofre, whether or not the product is actually crosslinked is immaterial. Its ultimate performance as a fluff pulp has been greatly enhanced by the low temperature glycol/dialdehyde treatment. The sheeted cellulosic web can be treated at a number of locations available on conventional papermaking machinery. Preferably it is treated about midway through the wet press section of the paper machine. However, equally suitable results are obtained by treatment following the press section or at a downstream location such as a size press, if one is available, or by the use of a post dryer treatment. The moisture content of the web can be in the range of 3–50% at the time of treatment with the solution of the glycol and dialdehyde. Preferably the moisture content is greater than about 30% at the time of treatment.

Glycols may be selected from a group which are readily available commercially. The particular glycol does not appear to be critical. Materials such as ethylene glycol, diethylene glycol, polyethylene glycol having a molecular weight less than about 30,000, propylene glycol, and dipropylene glycol are all suitable.

The dialdehyde may be chosen from the group of materials which are preferably aliphatic in nature and include materials such as glyoxal, glutaraldehyde and alpha-hydroxyadipaldehyde. Glyoxal is a preferred dialdehyde because of its relatively low cost and ready commercial availability.

The molar ratio of glycol to dialdehyde is not particularly critical. Generally it will be in the ratio of 1:3 to 3:1. In some cases superior results were seen when the two additive chemicals were present in a molar ratio of about 1:1.

It appears that the glycol is especially effective in increasing the absorbency rate of a fluff product made from the treated fiber. The dialdehyde may serve in some capacity to chemically link the glycol to the cellulose although the exact mechanism is not known.

It is an object of the present invention to provide a method of making a resilient hydrophilic cellulose pulp which can be mechanically formed into a fibrous fluff having an increased water absorption rate.

It is also an object of the present invention to make a cellulosic fluff pulp which can be conveniently produced on existing papermaking equipment without significant loss of production rate.

It is a further object of the present invention to provide a pulp having increased water absorption rate which is not brittle and can be readily converted into a fluff product on conventional equipment without generation of excessive amounts of fiber fines.

It is another object to produce a dialdehyde/glycol treated fluff pulp product which requires no acidic catalyst and need not be heat cured at temperatures in excess of 100° C.

It is yet another object of the invention to provide absorbent fluff products made with the treated pulp.

DESCRIPTION OF THE PREFERRED EMBODIMENTS

In a disposable absorbent fluff product such as a diaper or sanitary napkin, a number of physical mechanisms are at work. The product must be able to rapidly absorb discharged liquid to prevent flooding and leakage. The fluff must also serve by capillarity to distribute the discharged liquid throughout the product in order to achieve the maximum holding capability. Finally, the fluff itself must be able to retain the discharged liquid without leakage under loads imposed by the body of the wearer. Of the just-described characteristics, a high absorption rate is perhaps the most critically important.

So-called fluff pulps may be produced by any of the well known pulping processes. Those sold in the United States are most typically made from Southeastern or Northwestern softwoods by the kraft process. Pulps produced by the sulfite process and thermomechanical pulps are also used for production of fluff-based products. It is virtually universal that the pulp manufacturer sells the sheeted product in rolls to the convertor. The fluff is made by milling the sheets in the convertor's plant at the point of manufacture of the ultimate absorbent product. The milling operation, normally using a hammermill of some kind, is relatively high in energy consumption. For this reason, and because some convertors have pinmill fiberizers or lack hammermills of sufficient power, some pulp manufacturers supply products treated with a softener or debonding agent. These are typically quaternary ammonium compounds of some sort. One anionic softening system is taught is Laursen, U.S. Pat. No. 4,303,471. Softening agents may reduce the power required for milling a sheet into fluff, but they are not without their drawbacks since they adversely affect liquid absorption characteristics. In particular, the absorption rate of a softened pulp may be only half to two thirds that of an untreated pulp. This is a price many convertors are not willing to pay since it adversely affects their product performance.

The prior art has suggested the use of crosslinked cellulosic fiber for the manufacture of disposable absorbent products. Again, as in the case of Bernardin, U.S. Pat. No. 3,244,926, this would usually involve a cumbersome and expensive heat curing step that would also, for all practical purposes, have to be carried out in the converter's plant. This is an inconvenience and expense the converters have not been willing to tolerate. The alternative, where a crosslinked sheet was heat treated by the producer, has been equally unattractive because the embrittled pulps produce an excessive and unacceptable amount of fines when milled into a fluff.

The present method is further advantageous in that no formaldehyde containing compounds are involved which could subsequently result in irritating and/or toxic fumes being liberated during a later stage of conversion or from the ultimate product.

The method of the present invention and the products prepared by the method can be readily understood by reference to the following examples.

EXAMPLE 1

The following procedure was used to make laboratory handsheets for evaluation. A 25 g (dry weight) sample was reslurried in about 8400 mL of water and formed into a sheet on a standard 8×8 inch (203×203 mm) Noble and Wood laboratory sheet mold, using a 150 mesh stainless steel screen. The sheet was removed and pressed between synthetic fiber felts so that moisture content was reduced to about 50%.

A solution of the desired amount of 45% aqueous glyoxal and a glycol was made in sufficient water to make 25 mL. Twice the ultimately desired amounts of glyoxal and glycol were used to accommodate subsequent losses. This solution was uniformly spread on the pressed handsheet and sufficient time allowed for absorption. The treated handsheet was then again pressed as before and dried on a Noble and Wood laboratory drum dryer to the range of about 3–12% residual moisture.

Chemical pickup was determined by comparing the dry weight of a treated sheet with that of an untreated control.

EXAMPLE 2

The following procedure was used for making mill-scale trials for evaluation. Either a temporary hand held or a fixed shower bar was used to continuously apply the desired level of glyoxal/glycol to the moving sheet. The spray from the nozzles of the shower provided even and uniform coverage of the pump sheet. It is necessary to have uniform distribution through the sheet as well as across the sheet. Another criterion of the process is application without significant loss of chemicals. These goals were best met by application of the chemical solution in the wet-end press section of the paper machine. The 45% glyoxal solution and glycol were mixed and diluted with an equal volume of water. This solution was pumped to the shower bar with pump delivery being controlled to give the desired application rate.

Satisfactory results were attained without excessive increase in sheet moisture by applying the chemical mixture just prior to either the first, second, or third press sections or just after the third press section. Best results with the particular equipment used for the trials were attained with solution application just before the sheet entered the second press section. Chemical retention for solution application at this point was about 95% of that applied.

The glyoxal/glycol solutions are quite acidic and at a pH of about 2. Sheet pH prior to application was about 5.5–6. This pH dropped about 1 full unit to 4.5–5 following glyoxal/glycol application.

Treated pump was dried normally to a final moisture content of about 5%. At no time did the sheet temperature exceed 100° C.

EXAMPLE 3

Fluffed pulp samples were tested for absorptive capacity and absorption rate by the procedure outlined by Martinis et al., *Proceedings*, Tappi Annula mtg. (Chicago): 133–140 (Mar. 2–5, 1981). This paper is herein incorporated by reference. Briefly stated, sheeted pulp is torn into small pieces and fluffed as 2 g charges for 30 seconds in a Waring Blender at 20,000 rpm and conditioned at 22° C. and 50% RH for about four hours prior to testing.

The conditioned fluff is fed through an opposed rotating pin dispersion device into a tube through which it descends by gravity and suction in a downward, essentially laminar, airflow. The fluff is deposited in a relatively much shorter screen bottomed tube in which it is subsequentially handled and tested. The sample tube has a cross-sectional area of 25 $cm^2$. Sample tubes can accommodate varying weights of fluff but 4 g samples are most typical.

After removing the sample tube and contained sample from the former, dry bulk density can be readily determined at various compressive loadings. A plunger riding on the sample can be locked at a specific height to control sample density. Alternatively, the plunger carrying any specific weight can be allowed to free float on the fluff sample. The plunger itself weighs 150 g and exerts a force of 0.6 kPa on the sample when no supplementary weights are used.

Most fluff samples are tested under loads of 2.5 kPa or at a constant fluff density of 75 kg/$m^3$ (0.075 g/$cm^3$). Resiliency is determined by removing all weight from the sample and noting any springback.

The bottom of the fluff sample, still retained in the sample tube under the specified load, is allowed to contact water held at constant level in a container. An electrical contact on the screen supporting the sample starts a timer when the water contacts the bottom of the fluff. A similar contact on the loading plunger stops the timer when the top of the sample is wet by capillary rise. After 30 seconds, the water container is drained and the height of the wetted fluff is measured. The sample is then weighed and liquid capacity calculated.

EXAMPLE 4

To show the effect of different glycols on aborbency rate and water holding capacity of treated pulps a series of tests was made using five linear glycols of different chemical composition. Glycols were used in amounts of 20 and 50 kg/t along with 67.5 kg/t glyoxal except for the control sample. All tests were on 8×8 inch handsheets made as described before and using a bleached mixed northwestern softwood kraft pulp as furnish. The control pump had no chemical treatment. Results are in the following table.

TABLE I

| Glycol | Usage kg/t | Absorbency Rate mm/sec | Water Capacity, g water/g pulp |
|---|---|---|---|
| None | 0 | 3.2 | 14.1 |
| Ethylene | 20 | 2.9 | 13.4 |
|  | 50 | 4.5 | 13.7 |
| Diethylene | 20 | 4.5 | 15.0 |
|  | 50 | 5.7 | 14.4 |
| Polyethylene* | 20 | 4.5 | 15.4 |
|  | 50 | 5.7 | 14.4 |
| Propylene | 20 | 4.2 | 15.1 |
|  | 50 | 5.9 | 14.5 |
| Dipropylene | 20 | 5.5 | 15.0 |
|  | 50 | 6.2 | 14.4 |

*Molecular weight~1,000

It is clearly evident that all of the glycols improve absorbency rate significantly. However, in all but one case the higher level of glycol usage adversely affected water holding capacity by about 4-7%.

EXAMPLE 5

In order to more precisely determine the effect of glycol usage, a series of handsheets was made as in Example 4 using only diethylene glycol at levels between 5 and 40 kg/ton of dry pulp fiber. Test results are given in Table II.

TABLE II

| Diethylene Glycol kg/t | Glyoxal kg/t | Absorbency Rate mm/sec. | Water Capacity g water/g pulp |
|---|---|---|---|
| 0 | 0 | 3.2 | 14.1 |
| 30 | 0 | 4.7 | 13.5 |
| 0 | 6.75 | 4.2 | 15.9 |
| 5 | 6.75 | 4.6 | 16.0 |
| 10 | 6.75 | 4.7 | 16.0 |
| 15 | 6.75 | 5.1 | 16.1 |
| 30 | 6.75 | 5.4 | 14.9 |
| 40 | 6.75 | 5.8 | 15.2 |

Both the glycol and glyoxal by themselves improve absorbency rate and water holding capability. However, the effects of the two appear to be additive. Optimum properties are reached at an approximate 1:1 mole ratio fo glycol:glyoxal.

EXAMPLE 6

The improved wicking properties of the glycol/-glyoxal treated pulps extend beyond faster wicking rates. Ultimate wicking height is much greater in the treated pulps than in untreated. Tests were made as in Example 2 in a northwestern pulp mill on a mixed softwood bleached kraft pulp and in a southeastern pulp mill on a similar pulp made from southern pine. Chemical application was 15 kg/t of 45% glyoxal (6.75 kg/t on 100% basis) and 20 kg/t propylene glycol. This is an approximate 1:1 mole basis.

For these tests it was necessary to modify the test procedure of Example 3 somewhat. For every 20 mm of wicking height anticipated 4.0 grams of pulp was used at test density of 0.08 g/cm$^3$. Thus to measure a liquid rise of 60 mm a 12.0 g fluff sample would be used for the test.

Result of tests are given in Table III.

TABLE III

| | Wicking Time to Achieve Given Wicking Heights | | | |
|---|---|---|---|---|
| | Wicking Time, Sec. | | | |
| Wicking | Southern Pine | | Northwestern Softwood | |
| Height, mm | Untreated | Treated | Untreated | Treated |
| 20 | 3 | 2 | 4 | 3 |
| 40 | 20 | 12 | 19 | 12 |
| 60 | 62 | 36 | 60 | 34 |
| 80 | 127 | 69 | 323 | 84 |
| 100 | — | 171 | — | 169 |
| 120 | — | 710 | — | 349 |

The data of the above table can also be expressed with wicking time being the independent variable, as shown in Table IV.

TABLE IV

| | Wicking Height vs. Time | | | |
|---|---|---|---|---|
| | Wicking Height, mm | | | |
| Wicking | Southern Pine | | Northwestern Softwood | |
| Time, sec. | Untreated | Treated | Untreated | Treated |
| 30 | 48 | 56 | 42 | 58 |
| 60 | 62 | 72 | 54 | 75 |
| 180 | 86 | 104 | 78 | 110 |
| 360 | 88 | 123 | 81 | 136 |

All of the above tests were run at a fluff density of 0.08 g/cm$^3$. The obvious wicking superiority of the treated pulps is also clearly apparent when tests are run at other fluff densities as is seen in Table V.

TABLE V

| | Wicking Height vs. Fluff Density[1] | | |
|---|---|---|---|
| Fluff Density, gm/cm$^3$ | Pine, Untreated | Pine, Treated | Northwestern, Treated |
| 0.06 | 44 | 60 | 77 |
| 0.08 | 88 | 123 | 136 |
| 0.10 | 105 | 146 | 142 |

[1]At 360 seconds wicking time.

EXAMPLE 7

Over 40 samples of different commerically available fluff pulps were tested for absorbency characteristics, as described in Example 3. These were compared with samples similar to those made in Example 6, using a glyoxal/propylene glycol treated northwestern mixed softwood bleached kraft pulp (about 80% Douglas-fir) and a similarly treated southern pine bleached kraft pulp.

Results were as follows:

TABLE VI

| | Absorbency Rates, mm/sec. | | |
|---|---|---|---|
| | No of Samples | Range | Average |
| Mixed type softened pulps[1] | 8 | 1.5–2.5 | 2.2 |
| Thermomechanical pulps | 1 | — | 2.0 |
| Southern pine pulps | 19 | 2.5–4.5 | 3.7 |
| Sulfite pulps | 12 | 1.5–4.5 | 2.7 |
| Douglas-fir pulps[2] | 6 | 1.0–4.5 | 3.8 |
| Northwest softwood, untreated | 1 | — | 3.0 |
| Northwest softwood treated | 1 | — | 6.0 |

TABLE VI-continued

| | Absorbency Rates, mm/sec. | | |
|---|---|---|---|
| | No of Samples | Range | Average |
| Southern pine, treated | 1 | — | 8.0 |

[1]Treated with quaternary ammonium debonding agent.
[2]Mixed northwestern furnish, predominately Douglas-fir.

TABLE VII

| | Water Holding Capacity, g H$_2$O/g Pulp | | |
|---|---|---|---|
| | No Samples | Range | Average |
| Mixed type softened pulps | 7 | 12.0–12.5 | 12.2 |
| Thermomechanical pulp | 1 | — | 11.0 |
| Southern pine pulps | 21 | 11.5–13.5 | 12.3 |
| Sulfite pulps | 12 | 13.0–14.0 | 13.4 |
| Douglas-fir pulps | 6 | 11.0–13.5 | 12.8 |
| Northwest softwood, untreated | 1 | — | 13.0 |
| Northwest softwood, treated | 1 | — | 14.5 |
| Southern pine, treated | 1 | — | 13.5 |

The superior performance in both absorption rate and holding capacity of the treated pulps is readily apparent when compared with those presently available in the marketplace.

EXAMPLE 8

Consumption of power required to fiberize sheeted pulps is a significant expense and can be a limiting factor in the production of diapers and related products. It is a principal reason for the treatment during production of pulps treated with quaternary softening or debonding agents. However, savings in fiberization power must be balanced against the poorer absorbency of softened pulps. This may require the use of heavier fluff batts to compensate for reduced absorbency.

Fiberization energy was measured by recording sheeted pulp feed rate and motor current as the pulp was fed into a 406 mm (16 in.) fixed hammer hammermill operated at 3,000 rpm by a 150 hp motor.

Knots (unseparated fiber bundles) are determined by screening a sample of fluff through a stack of five standard 203 mm (8 inch) diameter Tyler screens, using a downward air flow of 0.42 m$^3$/min. (15 cfm). The air column is vibrated vertically at 15 hz by an acoustical transducer. Material retained on 5, 8, and 12 mesh screens is considered as knots. That captured on a 60 mesh screen is the most desirable fiber while that retained on or passing through a 200 mesh screen is considered as fines. A typical unsoftened market pulp will have about 20–25% knots and 10–20% fines after fiberization. The knots will usually be in the 10–15% range with softened (or debonder treated) pulps.

Samples of untreated and glyoxal/glycol treated fir and pine pulps were prepared in mill trials as described in Example 2. The fir was treated with 5.62 kg/t glyoxal (100% basis) and 12.5 kg/t propylene glycol. Pine pulp was treated with 6.75 kg/t glyoxal and 15 kg/t propylene glycol. Fiberization energy and efficiency are reported in Table VIII.

TABLE VIII

| | Fiberization Energy, kJ/kg | Fiberization Effic. (Knots), % |
|---|---|---|
| Pine, untreated | 320 | 20 |
| Pine, treated | 290 | 14 |
| Fir, untreated | 270 | 35 |
| Fir, treated | 240 | 27 |

The improved fiberization characteristics of the treated pulps are apparent. These improvements are not as great as would be expected by the use of debonding agents with untreated pulps.

EXAMPLE 9

A test was made using glutaraldehyde and propylene glycol to treat a northwest softwood pulp. Handsheets were made as in Example 1. The following results were obtained.

TABLE IX

| Sample Treatment | Dialdehyde Usage, kg/t | Glycol Usage, kg/t | Absorbency Rate, mm/sec. | Capacity g/g |
|---|---|---|---|---|
| None | 0 | 0 | 2.7 | 13.3 |
| Glyoxal | 9 | 0 | 3.1 | 14.6 |
| Glutaraldehyde | 20 | 0 | 3.2 | 13.7 |
| Glutaraldehyde[1] | 5 | 6.5 | 3.7 | 13.5 |
| Glutaraldehyde[1] | 10 | 13 | 3.9 | 13.1 |

[1]Molar ratios of glutaraldehyde to glycol is 1:1.7.

The higher molecular weight dialdehyde used with propylene glycol appears to be as effective as glyoxal at improving absorption rate. However, glutaraldehyde gives only minor improvement in absorption capacity and may be less effective than glyoxal in this regard. An approximate 1:1 molar ratio of dialdehyde to glycol might give better absorbent capacity results than are seen above, if an analogy with glyoxal is valid.

It will be evident to those skilled in the art that many variations and changes can be made without departing from the spirit of the invention. It is the intention of the inventors that the scope of the invention should be limited only by the following claims.

I claim:

1. A method of making a resilient hydrophilic cellulose fluff product which comprises:
   sheeting a fibrous cellulosic material from an aqueous slurry into a fibrous web;
   treating the web with an aqueous solution of a glycol and dialdehyde wherein the glycol is of the type HO—[(CH$_2$)$_m$O]$_n$—H where m is 2 or 3 and n is in the range 1–500, and the dialdehyde is of the type OCH—(CHX)$_n$—CHO where n is in the range of 0–4 and X is hydrogen or hydroxyl, said glycol being applied in an amount in the range of 5–50 kg/t of fiber and the dialdehyde being applied in the range of 5–50 kg/t;
   drying the treated web to a moisture content in the range of about 1–20% to react the cellulosic material with the dialdehyde, and
   mechanically defiberizing the dried treated sheet and air felting the fiber into an absorbent fluff product.

2. The method of claim 1 which further includes incorporating the absorbent fluff product into a disposable diaper.

3. The method of claim 1 which further includes incorporating the absorbent fluff product into a sanitary napkin.

4. The absorbent fluff product formed by the method of claim 1.

5. The disposable diaper formed by the method of claim 2.

6. The sanitary napkin formed by the method of claim 3.

7. A resilient hydrophilic modified cellulose pulp which comprises the product formed by:

sheeting a fibrous cellulosic material from an aqueous slurry into a fibrous web;

treating the web with an aqueous solution of a glycol and dialdehyde wherein the glycol is of the type $HO-[(CH_2)_mO]_n-H$ where m is 2 or 3 and n is in the range of 1–500, and the dialdehyde is of the type $OCH-(CHX)_n-CHO$ where n is in the range of 0–4 and X in hydrogen or hydroxyl, said glycol being applied in an amount in the range of 5–50 kg/t of dry fiber and the dialdehyde being applied in the range of 5–50 kg/t; and drying the treated web to a moisture content in the range of about 1–20% to react the cellulose with the dialdehyde, wherein the resulting dried sheeted product has the property that it can be mechanically defibered into a fibrous fiber without excessive fiber brokerage, said fluff having an increased water absorption rate when compared with a similar fluff made from an untreated pulp.

* * * * *

UNITED STATES PATENT AND TRADEMARK OFFICE
CERTIFICATE OF CORRECTION

PATENT NO. : 4,853,086
DATED : Aug. 1., 1989
INVENTOR(S) : Peter A. Graef

It is certified that error appears in the above-identified patent and that said Letters Patent is hereby corrected as shown below:

In column 2, line 33, "not" should read --note--;

In column 2, line 38, "direct" should read --directed--;

In column 3, line 16, "pump" should read --pulp--;

In column 3, line 56, "beofre" should read --before--;

In column 5, line 7, "taught is" should read --taught in--;

In column 5, line 19, "3,244,926" should read --3,224,926--;

In column 5, line 66 "pump" should read --pulp--;

In column 6, line 22, "pump" should read --pulp--;

In column 7, line 7, "67.5 kg/t" should read --6.75 kg/t--;

In column 7, line 11, "pump" should read --pulp--;

In column 7, line 49, "5.8" should read --5.6--;

UNITED STATES PATENT AND TRADEMARK OFFICE
CERTIFICATE OF CORRECTION

PATENT NO. : 4,853,086
DATED : Aug. 1, 1989
INVENTOR(S) : Peter A. Graef

It is certified that error appears in the above-identified patent and that said Letters Patent is hereby corrected as shown below:

In column 12, line 12, "fibrous fiber" should read --fibrous fluff--.

Signed and Sealed this

Nineteenth Day of June, 1990

Attest:

HARRY F. MANBECK, JR.

*Attesting Officer*  *Commissioner of Patents and Trademarks*